(12) United States Patent
Grabosch

(10) Patent No.: US 9,113,978 B2
(45) Date of Patent: Aug. 25, 2015

(54) IMPLANT FOR INSERTION INTO THE JAWBONE, PROSTHETICS PILLAR AND IMPLANT SYSTEM

(75) Inventor: Reinhold Grabosch, Munich (DE)

(73) Assignee: HELIOCOS GmbH, Stuttgart (DE)

( * ) Notice: Subject to any disclaimer, the term of this patent is extended or adjusted under 35 U.S.C. 154(b) by 0 days.

(21) Appl. No.: 12/737,518

(22) PCT Filed: Jul. 21, 2009

(86) PCT No.: PCT/EP2009/005289
§ 371 (c)(1), (2), (4) Date: Jan. 20, 2011

(87) PCT Pub. No.: WO2010/009866
PCT Pub. Date: Jan. 28, 2010

(65) Prior Publication Data
US 2011/0123952 A1    May 26, 2011

(30) Foreign Application Priority Data
Jul. 21, 2008   (DE) .................. 10 2008 035 070

(51) Int. Cl.
*A61C 8/00* (2006.01)

(52) U.S. Cl.
CPC ............... *A61C 8/0018* (2013.01); *A61C 8/005* (2013.01); *A61C 8/0039* (2013.01)

(58) Field of Classification Search
CPC .. A61C 8/0018; A61C 8/0033; A61C 8/0034; A61C 8/0039; A61C 8/005
USPC ...................................... 433/172–175, 201.1
See application file for complete search history.

(56) References Cited

U.S. PATENT DOCUMENTS

| | | | |
|---|---|---|---|
| 3,435,526 A | | 4/1969 | Brancato |
| 3,708,883 A | * | 1/1973 | Flander .......................... 433/174 |
| 4,738,062 A | | 4/1988 | Dickey |
| 4,947,502 A | | 8/1990 | Engelhardt |
| 5,447,435 A | * | 9/1995 | Brodbeck ...................... 433/173 |
| 5,489,210 A | * | 2/1996 | Hanosh ......................... 433/173 |
| 5,735,898 A | * | 4/1998 | Bråemark .................. 623/11.11 |
| 5,885,079 A | * | 3/1999 | Niznick ......................... 433/174 |
| 5,899,940 A | * | 5/1999 | Carchidi et al. .............. 606/305 |
| 6,007,337 A | * | 12/1999 | Bauer ............................ 433/173 |
| 6,129,763 A | * | 10/2000 | Chauvin et al. ............ 623/17.11 |
| 6,213,775 B1 | * | 4/2001 | Reipur .......................... 433/173 |
| 6,217,331 B1 | * | 4/2001 | Rogers et al. ................. 433/173 |
| 6,371,989 B1 | * | 4/2002 | Chauvin et al. ............ 623/17.11 |
| 7,300,282 B2 | | 11/2007 | Sapian |
| 7,628,814 B2 | * | 12/2009 | Studer et al. ............... 623/17.11 |
| 8,231,387 B2 | | 7/2012 | Salvi et al. |
| 2003/0009235 A1 | * | 1/2003 | Manrique et al. .......... 623/23.63 |
| 2005/0042574 A1 | * | 2/2005 | Lazarof ........................ 433/174 |
| 2005/0164146 A1 | | 7/2005 | Cantor |

FOREIGN PATENT DOCUMENTS

| | | |
|---|---|---|
| CH | 684384 | 9/1994 |
| DE | 665805 | 10/1938 |

(Continued)

*Primary Examiner* — Cris L Rodriguez
*Assistant Examiner* — Hao D Mai
(74) *Attorney, Agent, or Firm* — Pandiscio & Pandiscio, P.C.

(57) ABSTRACT

An implant for insertion into the jawbone, the implant including a helical body for receiving at least part of a prosthetics pillar, the prosthetics pillar configured for insertion into the implant, the prosthetics pillar comprising a screw section with an external thread, and the prosthetics pillar further configured to carry an artificial tooth.

14 Claims, 2 Drawing Sheets

(56) References Cited

FOREIGN PATENT DOCUMENTS

| EP | 0263809 | 4/1988 |
|---|---|---|
| GB | 2416996 | 2/2006 |
| JP | 8-644 | 1/1996 |
| JP | 2008-93426 | 4/2008 |
| WO | WO-99/17676 | 4/1999 |
| WO | WO 2008/052300 | 5/2008 |

\* cited by examiner

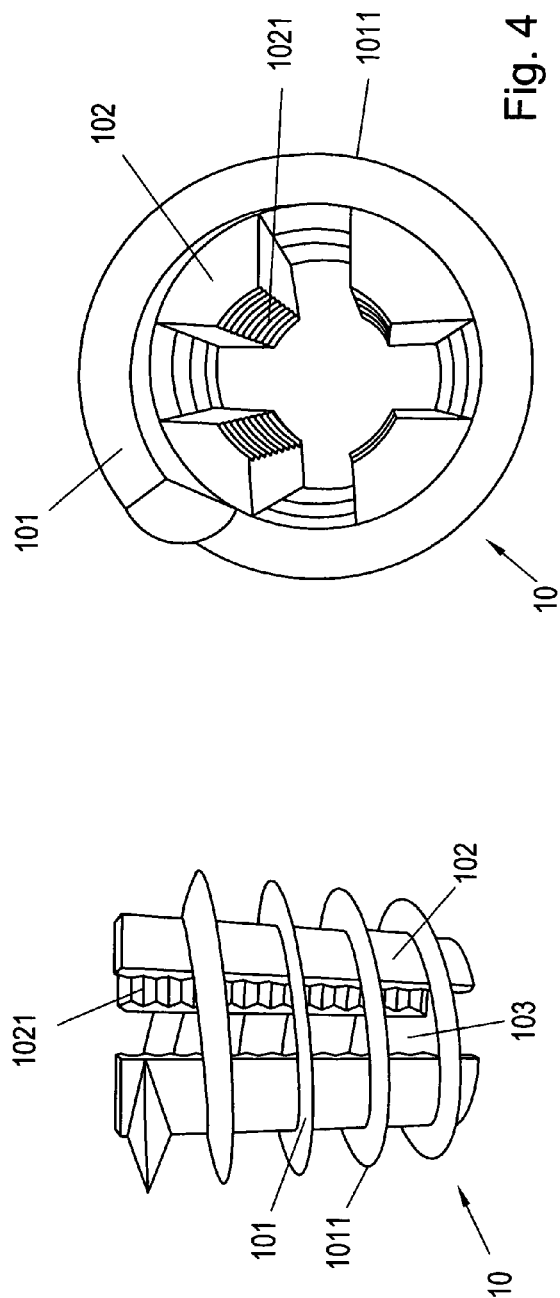

IMPLANT FOR INSERTION INTO THE JAWBONE, PROSTHETICS PILLAR AND IMPLANT SYSTEM

FIELD OF THE INVENTION

The present invention relates to an implant for insertion into the jawbone, a prosthetics pillar as well as to an implant system.

BACKGROUND OF THE INVENTION

Only an entirely toothed, healthy dentition ensures the entire functionality of the mastication organ. By extraction of a tooth an osseous alveolus or gap is generated, which collapses during healing and leaves a defect in the jawbone. The thus resulting gap should be provided with an implant and should be closed as soon as possible. Implants known to date in prosthodontics, however, have the disadvantage that the extraction area in general can only be provided with an implant after half a year. So far the utilization of bone deposition techniques or bone augmentation is necessary for the implantation, to provide a sufficient implant bed. After the surgical insertion of the artificial tooth root into the jawbone the wound then needs another several weeks of absolute rest, so that the surrounding jawbone and the gum can closely adjoin to the implant.

The problem to be solved by the present invention is to provide a solution, which allows for the tending of the tooth bed immediately after the extraction of the tooth as well as a facilitated and reliable replacement of a tooth by an artificial tooth. In addition, the period of time necessary for the replacement of the extracted tooth should be minimized.

SUMMARY OF THE INVENTION

One finding that the present invention is based on is that this problem can be solved by providing an implant system wherein the section of the implant system which after implantation is enclosed by the jawbone, consists of two detachable parts.

According to a first aspect, this problem is solved by an implant according to claim 1. The implant for insertion into the jawbone is characterized in that the implant comprises a helical body for receiving at least part of a prosthetics pillar.

By the helical or spiral shape of the body of the implant a number of advantages can be achieved. In particular, the helical shape of the implant can serve for guiding the implant during implantation. In particular, the implant can be screwed into the bone due to its helical or spiral shape. Furthermore the helical shape of the implant preferably provides gaps between the windings or coils of the helical shape. This open structure of the implant is advantageous as bone will be able to grow through the gaps of the implant thereby fixating it further. Finally, the helical shape of the implant provides a hollow inside of the implant where at least part of a prosthetics pillar can be received and held. Thereby the components of the implant system consisting of the implant and the prosthetics pillar are connected to each other well within the jaw bone. A connection point above the jaw bone, in particular above the gum is not necessary and hence infections can reliably be avoided. As the connection between the implant and the prosthetics pillar is positioned at a position close to the end of the implant system, the forces acting on this connection are minimized. Such forces may occur during attachment of the artificial tooth to the implant system as well as during usage of the artificial tooth after its placement. Due to its helical shape, the implant thus can serve as a socket for a prosthetics pillar to which an artificial tooth can be connected.

According to a preferred embodiment, the windings or coils of the helical body are kept in a predefined distance. In contrast to a spring, where the distance between the coils or windings changes under force, the implant preferably maintains a constant distance between the windings. Thereby, the advantages derived from the gap between the windings can reliably be used, e.g. the bone can reliably penetrate the implant.

The constant distance between the windings may be obtained by the material used for the implant. According to one embodiment, however, the implant comprises at least one support strut for supporting the windings of the helical body. The support strut or struts preferably extend parallel to the longitudinal axis of the helical body of the implant. In particular the struts may be provided on the inside of the windings of the helical body. If several struts are provided along the circumference of the inside of the helical body, the struts are arranged such that they do not abut to one another. By providing spacing between the struts, the penetration of the implant can still be ensured. The struts together with the helical body form a thread basket. Preferably the struts and helical body are manufactured from one piece. This means that the helical body and the struts are integrally formed and thus a strong connection between these parts of the implant is ensured. In addition to providing support for the windings of the helical body, the struts may serve additional purposes. For example, the part of the prosthetics pillar which is to be received in the implant may derive additional support from the struts.

According to one embodiment of the implant, the length of the implant is smaller or equal to the length of the tooth root of the tooth to be replaced. This measurement of the implant is advantageous, as the implant after implantation or insertion, will be enclosed by the jawbone and will not extend over the top of the jaw bone or the gum. Thereby the healing of the implant after insertion is improved.

Preferably the implant comprises an internal thread. The internal thread or female thread serves for connection of the implant with the prosthetics pillar. The internal thread may be formed by the windings of the helical body of the implant itself. In this case the inclination or slope of the windings of the helical body corresponds to the inclination or slope of the thread which is provided on the prosthetics pillar. Preferably the internal thread extends over the entire length of the helical body. Thereby the contact surface of the implant with a prosthetics pillar can be maximized.

According to a preferred embodiment, the internal thread is, however, formed on the inside of at least one support strut of the implant. In this case the support struts are arranged on the inner circumference of the helical body. By providing the internal thread on a part of the implant which is different to the helical body, the inclination or slope thereof can be different from the inclination or slope of the windings of the helical body. This is advantageous as the windings of the helical body will preferably be chosen to be at a steeper angle compared to the slope of the internal thread which is used for connecting the prosthetics pillar to the implant.

According to a preferred embodiment, the helical body of the implant has a conical shape. By decreasing the diameter of the implant from one end to the other, the insertion of the implant into a cavity in the jawbone is facilitated.

Preferably at least part of the windings of the helical body are formed as blades. The blades may be formed by providing sharp outer edges of the windings of the helical body. Alternatively, the blades may be formed by providing recesses or notches in the windings of the helical body, whereby the surface of the windings becomes rough and can grind into bone.

According to one embodiment the implant comprises on one end at least one cavity for receiving a screwing tool. The cavity may be formed by one or more grooves in the winding of the helical body at this end. Alternatively, the cavity may be formed by gaps between struts provided within the helical body. In either case, the providing of a cavity facilitates the insertion, in particular the screwing in of the implant into the bone. No additional tools or adapters are necessary.

According to a further aspect, the present invention relates to a prosthetics pillar as carrier of an artificial tooth for insertion into an implant according to the present invention. The prosthetics pillar is characterized in that it comprises a screw section with an external thread. The screw or screwing section is located at one end of the prosthetics pillar, in particular on the end opposite to the receiving area for the artificial tooth. The external thread allows for a screwing connection between the implant and the prosthetics pillar and thus allows for a secure connection between these two parts. The inclination of the external thread therefore preferably corresponds to the inclination of an internal thread of the implant.

The prosthetics pillar preferably comprises a shaft section adjacent to the screw section. The shaft section allows for the length of the prosthetics pillar to be longer than the mere screwing section and receiving section for the artificial tooth. In particular the shaft section covers the distance between the upper end of an implant inserted into the bone and the upper end of the jawbone. Preferably, at least one longitudinal groove is provided in the outside surface of the shaft section. The grooves serve as a protection against rotation, once the implant system is completely installed. In this respect, the grooves allow for bone material to grow in there and thus increase the security of a reliable fixation of the implant system in the bone.

According to a preferred embodiment, the length of the screw section of the prosthetics pillar is equal to the length of the implant. Thereby the entire length of the implant may serve as a support for the prosthetics pillar and tilting of the prosthetics pillar can be avoided.

According to another aspect, the invention relates to an implant system comprising an implant and a prosthetics pillar. The implant system is characterized in that the implant is an implant according to the invention and the prosthetics pillar is a prosthetics pillar according to the invention.

According to one embodiment the implant system further comprises a marker pin with a screw section with an external thread for temporary insertion into the implant of the implant system. As the implant of the implant system will be inserted into the jawbone and will be enclosed thereby, the marker pin offers the possibility for the surgeon to mark the position of the implant. The marker pin may for example be used for marking a position on a mask. Once the implant is securely held in the jawbone, the surgeon can then use the mask with the marking produced by the marker pin to locate the implant within the jawbone and to introduce the prosthetics pillar into the implant.

Features and advantages which are described with respect to the inventive implant also apply to the inventive prosthetics pillar and the inventive implant system and vice versa.

The present invention provides several advantages over known solution. In particular, it is possible to immediately tend the extraction alveolus and thus to avoid collapse of the bone compartment. As the implant according to the present invention does not have a continuous separation face or surface, it can easily and entirely be penetrated by the growing bone, in particular the spongiosa. Thereby a fixed and targeted growing in and thereby a rapid anchoring of the new implant system can be achieved.

Bone replacement material is not necessary. In addition the amount of instruments necessary can be reduced. Finally, the treatment is shorter.

Further advantageous embodiments of the invention are obvious from the dependent claims and the following description.

The main advantages of the present invention to the patient and the surgeon are that the implanting of the implant can be carried out atraumatic, in particular as the drilling of the jaw bone, which is necessary according to the prior art is not necessary. As the steps of providing the implant are minimized, the duration of the treatment is also minimized and may be reduced by up to 50% of the duration necessary for prior art implementations. The stability of the implant in the jawbone, i.e. the connection between the jawbone and the implant is considerably improved. In addition, no screw connection within the implant is necessary above the gum, i.e. in the oral cavity. Furthermore, the invention allows for the implant system and ultimately the artificial tooth to be positioned in the same direction as the natural, extracted tooth. This is possible as the implant is inserted into the bone compartment which is created by the extraction of the tooth. Due to the penetration of bone material through the implant, the rotation of the implant at a later state, in particular during insertion of the prosthetics pillar or after provisioning of the artificial tooth, can be avoided.

BRIEF DESCRIPTION OF THE DRAWINGS

The invention will hereinafter be described again with reference to the enclosed figures, wherein:

FIG. 3 shows a schematic side view of an embodiment of the inventive implant;

FIG. 4 shows a schematic top view of an embodiment of the inventive implant; and FIG. 5 shows a schematic side view of an embodiment of a marker pin.

DETAILED DESCRIPTION OF THE PREFERRED EMBODIMENT

Figure 1:
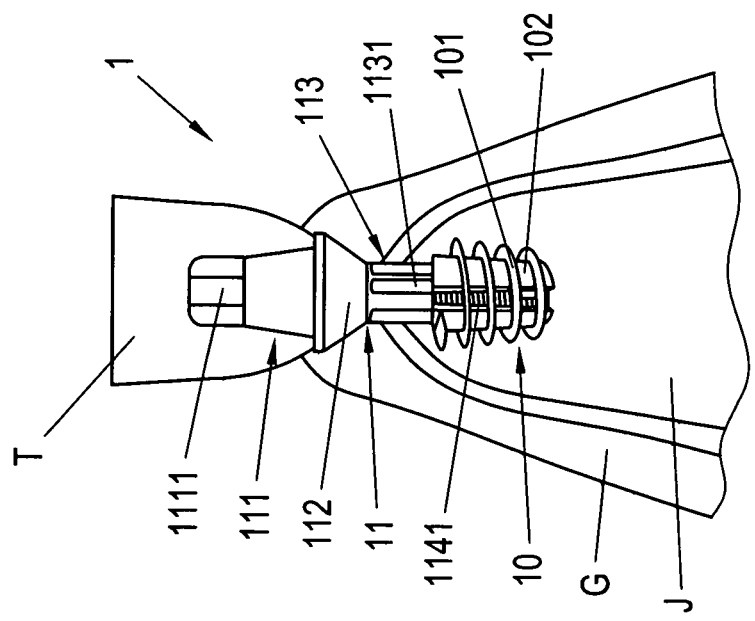
FIG. 1 shows a schematic sectional view of a jaw with an embodiment of the inventive implant system.

In FIG. 1 the top of a jawbone J which is surrounded by gum G is shown. In the jawbone J, where a tooth (not shown) has been extracted, an implant system 1 is inserted. Within the jawbone J the implant 1 is enclosed by the jawbone J. In the implant 1 a prosthetics pillar 11 is held. On top of the prosthetics pillar 11 an artificial tooth T is affixed.

The layout of the parts of the implant system 1 will now be described with respect to FIGS. 2 to 4. The implant 10 as depicted in FIG. 3 has a helical body 101 which is conically shaped. In the position shown in FIG. 3 the diameter of the helical body 101 increases from the bottom of the implant 1 to the top of the implant 1. The outer edges 1011 of the helical body 101 are formed as sharp edges and thus render the windings of the helical body 101 to be shaped as blades. On the inside circumference of the helical body 101 in the depicted embodiment, four support struts 102 are provided. They are connected or affixed to the windings of the helical body 101. As can be derived from the view in FIG. 4, the struts 102 have a wedge shape and are spaced from each other along the inner circumference of the helical body 101. Thereby, a thread basket is formed by the helical body 101 and the struts 102. In that basket openings 103 between the windings of the helical body 101 and the struts 102 are formed. At the inner side of the struts 102 grooves are provided which form an internal thread 1021. In the depicted embodiment, the slope of the internal thread 102 differs from the slope of the windings of the helical body 101. As four struts 102 of wedge shape are provided and are spaced from each other, a screw driver may be inserted into the gaps between the struts 102 and the implant 10 may thus be turned.

Figure 2:
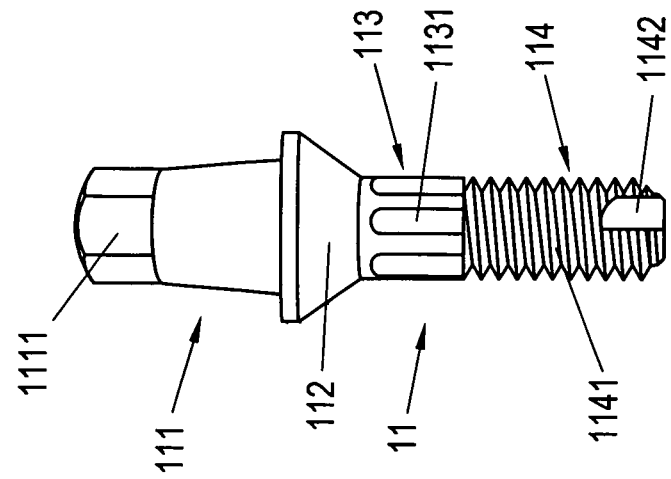
FIG. 2 shows a schematic view of an embodiment of the inventive prosthetics pillar.

The prosthetics pillar 11 as shown in FIG. 2 consists of a head portion 111, the top of which is formed as a screw head 1111. At the bottom of the head 111, a conical section 112 is provided. The diameter of the conical section 112 decreases from the head 111 towards a shaft section 113 adjacent to the conical section 112. In the shaft section 113 longitudinal grooves 1131 are introduced into the surface of the shaft section 113. The bottom part of the prosthetics pillar 11 is formed by a screw section 114. In this section, which is adjacent to the shaft section 113, an external thread 1141 is provided. At the end of the screw section 114 two notches 1142 are provided into the external thread 1141. These notches 1142 serve to facilitate insertion of the prosthetics pillar 11 into the implant 10.

In FIG. 5 a marking pin 12 is shown. The marking pin 12 has a cylindrical shape. At the bottom end an external thread 121 is provided on the marking pin 12. As shown in FIG. 5, a bushing 13 may be slipped onto the marking pin 12.

The insertion of the implant system into the jawbone will now be described. Immediately after extraction of the respective tooth (not shown), the implant 10 is screwed into the created osseous alveolus of the jawbone J. Once the implant 10 has been inserted into the jawbone, the marker pin 12 may be screwed into the implant via its screw section 121. A mask may be provided above the top of the gum G, e.g. between neighbouring teeth and the bushing 13 may be slipped onto the marking pin 12. Thereby or by other means the position of the implant 10 relative to the neighbouring teeth can be marked on the mask. The wound will provisionally be closed. The implanted implant 10 will rapidly and easily be penetrated by the bone growing, as it does not have a continuous separation face. Therefore the desired anchoring of the implant 10 in the jawbone J is stable within a short period of time. Once this condition has been achieved, the position of the implant 10 within the jawbone J can be identified by the mask or other means. Upon location of the implant 10, the prosthetics pillar 11 will be screwed into the implant 10 via its screw section 114 or screw dome. Once the screw section 114 is completely inside of the implant 10, the top of the conical part 112 of the prosthetics pillar 11 is close to the top of the gum G surrounding the jawbone J. The head 111 of the prosthetics pillar 11 extends over the gum G and the prosthetics pillar 11 is then available for the preparation of an artificial tooth T.

The present invention is not limited to the embodiment as shown in the figures. One form of the invention may be summarized as follows. The implant essentially has the form of a helical spring. The windings of the implant are kept in a specified distance to each other. In the embodiment the windings of the helical implant have a steady slope or inclination. In its longitudinal extension, the implant has conical shape. Thereby the implant being held at one end can be introduced into the osseous alveolus with its narrow end and due to its conicity can be screwed into the alveolus. The outer edge of the implant which extends from the first to the last winding is formed as a blade. Thereby the implant can be screwed like a wood screw into the osseous alveolus. The first winding at the broader end of the implant has one or several groves for form-locking contact with a screwing tool.

The implant according to the present invention preferably consists of Titanium, which is a material well accepted by the body of the patient. In a further embodiment, the implant consists of a solid material. In yet another embodiment, the implant consists of an elastic material.

The prosthetics pillar according to the present invention may also be referred to as a a suprastructure. The suprastructure preferably has a screw dome with an external thread as well as a head. The head may be made of porcelain or may be porcelain sintered because of esthetical and hygienic reasons, as it extends into the oral cavity where germs are present. The inclination of the external thread of the screw dome may be adapted to the inclination of the windings of the helical implant. The head of the prosthetics pillar may have a width over flats for a tool for screwing in the prosthetics pillar into the implant.

REFERENCE LIST 1 implant system
10 implant
101 helical body
1011 Outer edge
102 support strut
1021 internal threat
103 opening
11 prosthetics pillar
111 head
1111 screwhead
112 conical section
113 shaft
1131 groove
114 screw section
1141 external thread
1142 notch
12 marker pin
121 screw section
13 bushing
G gum
J jawbone
T artificial tooth

The invention claimed is:
1. Implant for insertion into a jawbone, the implant comprising a helical body for receiving at least part of a prosthetics pillar;
   wherein the helical body comprises:
      a plurality of turns defining a hollow body and separated by spaces therebetween, the spaces comprising openings extending into the hollow body, the openings being sized and configured to allow jawbone to grow through the spaces; and
      at least one support strut extending between at least two turns of the helical body for supporting the turns of the helical body, the at least one support strut made of a rigid material for keeping a predefined distance between the turns, and the at least one support strut extending along an inner surface of the helical body in a longitudinal direction of the implant;
   wherein the helical body and the at least one support strut are integrally formed;
   wherein at least part of the turns of the helical body are formed as blades; and wherein the implant comprises an internal thread, wherein the internal thread is formed on an interior surface of the at least one support strut.

2. Implant according to claim 1, characterized in that a length of the implant is smaller or equal to a length of a tooth root of a tooth to be replaced.

3. Implant according to claim 1, characterized in that the helical body has a conical shape.

4. Implant according to claim 1, characterized in that the implant comprises on one end at least one cavity for receiving a screwing tool.

5. The implant of claim 1 further comprising a prosthetics pillar as a carrier of an artificial tooth for insertion into the implant, characterized in that the prosthetics pillar comprises a screw section with an external thread.

6. The implant according to claim 5, characterized in that an inclination of the external thread corresponds to an inclination of the internal thread of the implant.

7. The implant according to claim 5, characterized in that the prosthetics pillar comprises a shaft section adjacent to the screw section, wherein at least one longitudinal groove is provided in an outside surface of the shaft section.

8. The implant according to claim 5, characterized in that a length of the screw section is equal to a length of the implant.

9. Implant system comprising an implant and a prosthetics pillar, characterized in that the implant comprises a helical body for receiving at least part of the prosthetics pillar and the prosthetics pillar comprises a screw section with an external thread;
  wherein the helical body comprises:
    a plurality of turns defining a hollow body and separated by spaces therebetween, the spaces comprising openings extending into the hollow body, the openings being sized and configured to allow jawbone to grow through the spaces; and
    at least one support strut extending between at least two turns of the helical body for supporting the turns of the helical body, the at least one support strut made of a rigid material for keeping a predefined distance between the turns, and the at least one support strut extending along an inner surface of the helical body in a longitudinal direction of the implant;
  wherein the helical body and the at least one support strut are integrally formed;
  wherein at least part of the turns of the helical body are formed as blades; and
  wherein the implant comprises an internal thread, wherein the internal thread is formed on an interior surface of the at least one support strut.

10. Implant system according to claim 9, characterized in that the implant system further comprises a marker pin with a screw section with an external thread for temporary insertion into the implant of the implant system.

11. A method for inserting an implant into a jawbone, the method comprising:
  extracting a tooth from the jawbone so as to create an opening in the jawbone;
  inserting an implant into the opening in the jawbone, the implant comprising a helical body, the helical body comprising a plurality of turns defining a hollow body and separated by spaces therebetween, the spaces comprising openings extending into the hollow body; wherein the helical body further comprises at least one support strut extending between at least two turns of the helical body for supporting the turns of the helical body; wherein the implant comprises an internal thread formed on an interior surface of the least one support strut of the helical body; wherein the implant is inserted into the jawbone so that the helical body does not extend above the jawbone and with a distance being between an upper end of the implant and an upper end of the jawbone, the distance being sized so that the implant will be enclosed by the jawbone; and
  inserting a prosthetics pillar into the implant, wherein the prosthetics pillar comprises a shaft having a screw section with an external thread at one end of the shaft and a portion for carrying an artificial tooth at the other end of the shaft, and further wherein the screw section of the prosthetics pillar is received within the helical body of the implant.

12. The method according to claim 11, further comprising inserting an artificial tooth onto the prosthetics pillar.

13. The method according to claim 11 wherein the prosthetics pillar further comprises a conical portion disposed between the screw section and the portion for carrying the artificial tooth, and further wherein, when the prosthetics pillar is inserted into the implant, the conical portion of the prosthetics pillar is positioned within the jawbone and the portion for carrying the artificial tooth extends out of the gum.

14. The method according to claim 11, further comprising inserting a marker pin into the implant in order to temporarily mark the position of the implant in the jawbone prior to inserting the prosthetics pillar into the implant.

* * * * *